United States Patent
Feistel (10) Patent No.: US 6,426,230 B1
(45) Date of Patent: *Jul. 30, 2002

(54) DISPOSABLE DIAGNOSTIC DEVICE AND METHOD

(75) Inventor: Christopher C. Feistel, Laguna Beach, CA (US)

(73) Assignee: Qualigen, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

This patent is subject to a terminal disclaimer.

(21) Appl. No.: 08/905,261

(22) Filed: Aug. 1, 1997

(51) Int. Cl.$^7$ ............................................... G01N 33/48
(52) U.S. Cl. ........................... 436/165; 422/102; 422/61
(58) Field of Search .................... 422/58, 61, 100, 422/102, 103; 436/164–166, 176–180, 808

(56) References Cited

U.S. PATENT DOCUMENTS

| | | | |
|---|---|---|---|
| 3,036,894 A | * | 5/1962 | Forestiere ..................... 422/61 |
| 3,689,224 A | | 9/1972 | Agnew et al. |
| 3,697,227 A | | 10/1972 | Goldstein et al. |
| 3,713,779 A | | 1/1973 | Sirago et al. |
| 3,726,645 A | | 4/1973 | Kaczmarek |
| 3,799,742 A | | 3/1974 | Coleman |
| 4,065,263 A | * | 12/1977 | Woodbridge ................. 422/61 |
| 4,588,554 A | | 5/1986 | Kaartinen et al. |
| 4,673,657 A | | 6/1987 | Christian |
| 4,806,316 A | | 2/1989 | Johnson et al. |
| 4,859,421 A | | 8/1989 | Apicella |
| 4,952,373 A | | 8/1990 | Sugarman et al. |
| 4,963,498 A | | 10/1990 | Hillman et al. |
| 5,031,797 A | | 7/1991 | Boris et al. |
| 5,057,285 A | | 10/1991 | Belt et al. |
| 5,061,446 A | | 10/1991 | Guigan |
| 5,077,010 A | * | 12/1991 | Ishizaka et al. ............... 422/56 |
| 5,132,087 A | | 7/1992 | Manion et al. |
| 5,154,888 A | | 10/1992 | Zander et al. |
| 5,200,152 A | | 4/1993 | Brown |
| 5,225,163 A | | 7/1993 | Andrews |
| 5,229,297 A | | 7/1993 | Schnipelsky et al. |
| 5,230,866 A | | 7/1993 | Shartle et al. |
| 5,254,479 A | * | 10/1993 | Chemelli ..................... 436/180 |
| 5,279,797 A | | 1/1994 | Burns et al. |
| 5,288,463 A | | 2/1994 | Chemelli |
| 5,290,518 A | | 3/1994 | Johnson |
| 5,294,404 A | | 3/1994 | Grandone et al. |
| 5,304,487 A | | 4/1994 | Wilding et al. |
| 5,422,271 A | * | 6/1995 | Chen et al. .................... 422/58 |
| 5,500,187 A | | 3/1996 | Deoms et al. |
| 5,609,828 A | | 3/1997 | O'Bear et al. |

FOREIGN PATENT DOCUMENTS

GB    2204398    8/1991

* cited by examiner

Primary Examiner—Lyle A. Alexander
(74) Attorney, Agent, or Firm—Rutan & Tucker LLP; Robert D. Fish (57) ABSTRACT

Disclosed is a disposable diagnostic device for conducting a diagnostic test on a sample. The device includes a substantially planar, flexible article, a channel formed within the article, at least one fluid-receiving compartment formed within the article and fluidly connectable to the channel, and a solid phase movably positioned within the channel. The article may be a laminate, and in particular, a laminate formed from two substantially planar, flexible sheets laminated together.

15 Claims, 10 Drawing Sheets

DISPOSABLE DIAGNOSTIC DEVICE AND METHOD

FIELD OF THE INVENTION

This invention relates to devices for conducting diagnostic tests and methods for using such devices. In particular, it relates to disposable diagnostic test devices, and methods for use of such devices.

BACKGROUND OF THE INVENTION

Advances in medical science have increased the need for clinical laboratory testing. The number of clinical laboratory tests performed is rapidly increasing every year. New tests and testing procedures are also expanding each year.

The medical field has relied on the clinical laboratory to perform these tests. Clinical laboratories depend on highly trained technical personnel and expensive equipment to perform the many tests needed by the medical community.

There is an ongoing need for disposable diagnostic products that reduce the complexities of operation and that can be used outside of the clinical laboratory, such as in the physician's office, emergency room, operating room, and at home. In addition, there is a continuing interest in performing individual tests in these localities. Desirable features for testing in these environments include operational simplicity, precision, reproducibility, relatively low costs, and increased safety in sample handling. It is desirable to have a disposable device that can be used for individual testing in these environments to meet these needs.

SUMMARY OF THE INVENTION

This invention provides a disposable diagnostic device used for conducting diagnostic tests, such as immunoassays, and a method for using this device to conduct such tests that can be performed outside of a clinical laboratory. The device is relatively easy to use and inexpensive to manufacture since it can be made using, for example, a simple lamination process. Formed within the device are multiple chambers used to conduct the diagnostic test. These chambers include a channel, through which a solid phase moves by application of a peristaltic force. Successive diagnostic fluids, such as reagents and washes, are then moved to and displaced from the solid phase, also by way of peristaltic forces. The solid phase is eventually moved to a region of the channel from which a test result is read.

In one aspect, the invention features a disposable diagnostic device for conducting a diagnostic test on a sample. The device includes a substantially planar, flexible article, a channel formed within the article, at least one fluid-receiving compartment formed within the article and fluidly connectable to the channel, and a solid phase movably positioned within the channel. The article is "flexible" in that the channel and fluid-receiving compartments within the article are sufficiently deformable to permit application of functional peristaltic forces as described below. Typically the entire article is fashioned from flexible material, although this need not be the case as long as the portions of the article defining the channel and compartments are sufficiently deformable.

In one embodiment, the article is a laminate, for example a laminate formed from two substantially planar, flexible sheets laminated together. A plurality of such articles can be manufactured as a continuous sheet capable of being wound into a roll. Users can easily remove individual articles from the roll by tearing at designated tear points, by cutting or by any other appropriate means of separation.

In yet other embodiments, the device includes a plurality of compartments formed within the laminate, also fluidly connectable to the channel. These compartments can be pre-filled with a fluid or empty, and can be aligned on opposite sides of the channel. The pre-filled compartments typically are filled with reagents and the empty compartments configured to receive waste fluids. The pre-filled compartments can be isolated from the channel by breakable seals. The solid phase can be manufactured from various materials, in various forms including without limitation beads, disks, stars, cubes, rods, and spheres.

The diagnostic device may be configured for application of a first peristaltic force for moving the solid phase along the channel, and for application of a second peristaltic force for moving fluid from the pre-filled compartment to the solid phase and from the solid phase to the empty compartment. As the fluid moves to and from the solid phase, the fluid movement can change direction along the solid phase as the solid phase moves along the channel.

In another embodiment, the channel may also include a sealable input port for application of a sample to the solid phase. A sample transfer device, that may be removable, and which is fluidly connectable to the input port for applying a predetermined quantity of sample to the solid phase, may also be included as part of the device. In addition, the channel can include an air vent that is connectable to an external source of gas for applying drying gas, e.g., air, to the solid phase.

In yet another embodiment, the diagnostic device includes a removable label that can be pre-printed with diagnostic test information, and adapted to receive patient information and test result data. Once removed, this label can be placed in the patient's medical file obviating the need for other manual or electronic transfer of the test data.

In another aspect of the invention, a method for conducting a diagnostic test, using the disposable diagnostic device described above, involves the steps of applying a sample to the solid phase, moving the solid phase along the channel by application of a first peristaltic force to the solid phase, moving a fluid from one compartment to the solid phase by application of a second peristaltic force to the compartment, allowing development of a diagnostic test result within the solid phase, and detecting the result. The first peristaltic force can be applied by movable dual pressures flanking the solid phase within the channel.

In preferred embodiments, the application of the second peristaltic force displaces fluid from the solid phase and the channel as the solid phase moves along the channel. The movement to and displacement from the solid phase can occur sequentially. As the movement and displacement occur, the fluid flow may change direction along the solid phase at least once as the solid phase moves along the channel. Generally, all fluids within the compartments are moved to the solid phase before detecting the result.

In other embodiments, the method involves the additional step of applying drying gas to the solid phase prior to detecting the result. Optionally, the solid phase can be agitated by moving the solid phase in a limited, repetitive back and forth motion within the channel.

When a label is included on the device, the method may also include the steps of recording test result data from the test result on a removable label adapted to receive the test data, recording patient information on the label prior to applying the sample, removing the label after the test result data have been recorded on it, and placing the label into the patient's medical file.

As described herein, the present invention has many advantages. First, the device as formed from flexible films (1) can be used in several orientations, (2) isolates the solid phase while allowing for solid phase movement, (3) provides for formation of incubation, wash and read chambers simply by the external application of pressure to the channel, and (4) provides a minimal mean diffusion path between solid phase-bound materials and reactive reagents in the fluid contacting the solid phase. In addition, the device provides a completely sealed testing system containing premeasured and prepackaged reagents, thereby preventing contamination of the testing reagents. The invention also eliminates pipet/dilutor dispensers, provides a unique sample aliquoting device, and provides a one step sample application of a measured volume of sample. Movement of the solid phase within the testing device facilitates washing by eliminating the need to wash the walls of the chamber in addition to washing the solid phase. Reversing the direction of fluid flow along the solid phase also improves the washing step. The device can include a dual purpose vent system that allows displacement of air within the chambers, as well as introduction of air for purging and drying situations.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE PREFERRED EMBODIMENTS

Figure 1:
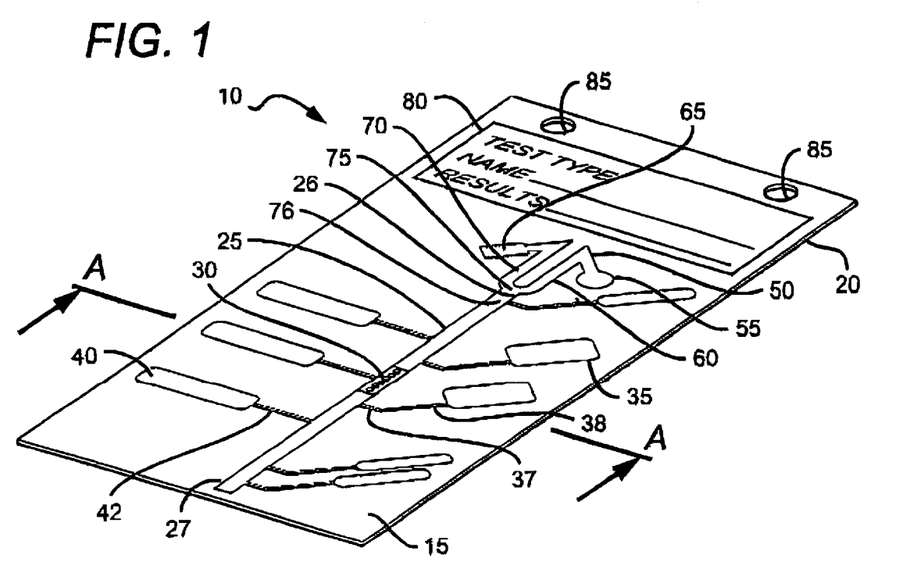
FIG. 1 is a perspective view of a disposable diagnostic device of the present invention.
Figure 2:
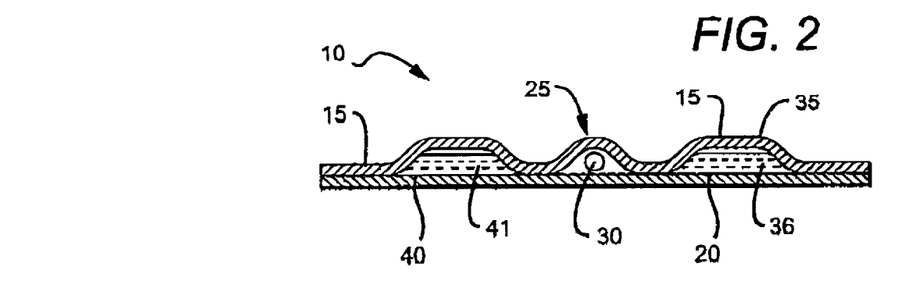
FIG. 2 is a cross-sectional view of the device of FIG. 1, taken along Line A—A.

FIG. 1 is a perspective view of a disposable diagnostic device 10 of the present invention for use in conducting a diagnostic test on a sample. FIG. 2 is a cross-sectional view of the device 10, taken along line A—A. The device 10 comprises an article, such as a laminate formed from a top sheet 15 and a bottom sheet 20, both substantially planar and flexible. The top 15 and bottom 20 sheets typically are formed from transparent or translucent thermoplastic material, including without limitation polypropylene, polyester, polyethylene, polyvinyl chloride, polyvinylidene chloride, and polyurethane.

Formed within the laminate is a channel 25 that extends along the length of the laminate from a sample transfer end 26 to a test result end 27. Enclosed within the channel 25 is a solid phase 30 that moves from the sample transfer end 26 to the test result end 27 during the course of the diagnostic test by external application of a peristaltic force (not shown). Hereinafter, with regard to directions within the channel 25, upstream is toward the sample transfer end 26, and downstream is toward the test result end 27. Although the channel 25 is straight in this embodiment, several channel shapes are contemplated, including circular and serpentine.

The solid phase 30 includes solid material in forms such as beads, particles, stars, disks, rods, cubes, spheres, membranes, or other suitable shapes. These forms can be present in various sizes and in various numbers, depending on the conditions desired for particular assay reagents and formats. The solid material can be any suitable material useful as a diagnostic solid phase, including without limitation polypropylene, polyester, polystyrene, polyurethane, nylon, styrene, glass, glass fiber, or thermoplastic. Generally, one or more specific binding reagents, or other reactants, are covalently or non-covalently coupled to the solid phase material. Typical specific binding reagents include polyclonal and monoclonal antibodies and functional fragments thereof, specific binding proteins such as avidin and biotin, and antigens capable of forming specific binding pairs with other specific binding reagents. Since a device 10 is fabricated to conduct a particular diagnostic test, the specific binding reagent used in the solid phase 30 is chosen to bind to a specific, desired analyte within the sample, thereby facilitating detection of that analyte in the particular diagnostic test being conducted.

Along the length of the channel 25 are also fluid-receiving compartments 35 and 40 formed within the laminate and fluidly connectable to the channel 25. At least one of these compartments 35 is pre-filled with a tracer or labeled reagent, wash, or other diagnostic test fluid, and at least one of the remaining compartments 40 is empty, waiting to receive waste fluids produced by the diagnostic test. Appropriate labeling reagents useful with the device 10 include without limitation fluorescent, calorimetric, chemiluminescent, enzymatic and radioactive markers. The pre-filled compartment 35 is fluidly connectable to the channel 25 via a passage 37 connecting the compartment 35 to the channel 25. Fluid 36 within the compartment 35 remains in the compartment 35 until pressure is externally applied to the compartment 35 by a peristaltic force (not shown). As a result, a breakable seal 38 is ruptured, releasing the fluid 36 into the channel 25 in the region of the solid phase 30.

The empty compartment 40 remains empty until fluid pressure forces the fluid 36 from the channel 25 into the empty compartment 40 through passage 42. The waste fluid 41 remains in the waste compartment 40 for later disposal of the device 10 in an appropriate manner. The pre-filled compartments 35 are arranged along one side of the channel 25 and the empty compartments 40 are arranged along the opposite side of the channel 25. However, other compartment arrangements are contemplated and within the scope of the claims.

A sample of bodily fluid, human or animal, or other testable material, is applied to the solid phase 30 within the channel 25 through a sample input area 50. A sample transfer device (not shown), such as a syringe, is used to apply the sample through an input port 55. Another embodiment of a sample transfer device includes a cylindrical cup that attaches to the input port 55. This cup is filled with sample fluid by a syringe or pipette, and then another cylindrical cup is placed in, and attached to, the first cup. The second cup is then pushed into the first cup, acting as a plunger, thereby forcing the sample fluid out of the first cup and into the sample input area 50 through the input port 55. Application of the sample under pressure forces the sample from the input port 55, along passage 60, through a "Y" intersection 75, up passage 70 and into a chamber 65. A breakable seal 76, located at the start of the channel 25, keeps the sample from moving down the channel 25, and instead directs the sample up the passage 70. Displacement of the sample in this manner results in a constant, known volume of sample being available in the "Y" intersection 75. Subsequent application of pressure to the "Y" intersection 75 causes the breakable seal 76 to rupture, thereby forcing the known volume of sample into the channel 25 in contact with the solid phase 30.

Device 10 also includes attachment holes 85 for mounting device 10 during a diagnostic test to, for example, a diagnostic test machine capable of applying and controlling the required peristaltic forces, and detecting the test results. Other suitable attachment devices or methods are also contemplated, for example hooks, loops and other mounting attachments coupled to the device 10 at appropriate locations.

A removable label 80 is also included to indicate the type of diagnostic test being conducted by the device 10, as well as patient information and test result data. The diagnostic test information is pre-printed on the label 80. Patient information is written, typed, or otherwise recorded onto the label 80 by the medical personnel performing the test, and test data are printed onto the label 80 by the diagnostic test machine, or by other means. This label 80 is removable and placeable in the patient's medical file, thereby eliminating the need for transferring data with attendant possibility for error.

Figure 3:
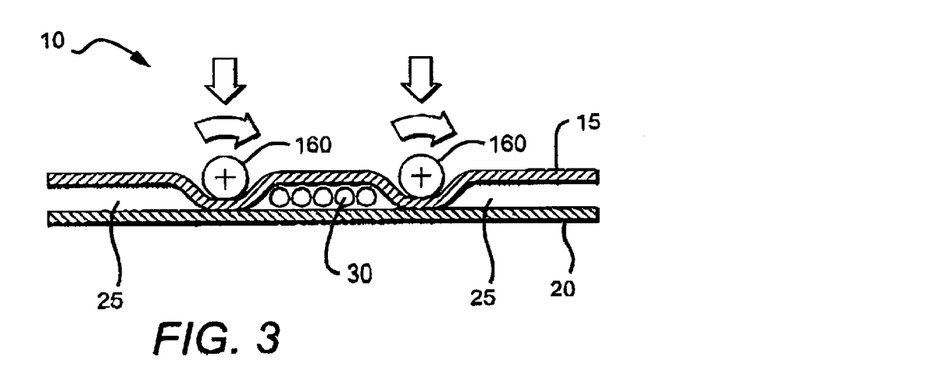
FIG. 3 is a side view of a portion of the device of FIG. 1 with external force applied.

FIG. 3 is a side view of a portion of the device 10 wherein a peristaltic force comprising external dual pressures 160 is applied to the channel 25. The dual pressures 160 flank the solid phase 30 by impinging the channel 25 directly upstream and downstream of the solid phase 30, thereby isolating the solid phase 30 from the remainder of the channel 25. The solid phase effectively fills the isolated portion of the channel, thereby minimizing the volume of fluid in contact with the solid phase. This volume minimization results in a minimal mean diffusion path between the solid phase-bound materials and the reactive reagents within the fluid contacting the solid phase. The dual pressures 160 move the solid phase 30 downstream in the channel 25 in a peristaltic manner by compressing the top sheet 15 against the bottom sheet 20 across the channel 25, thus pushing the solid phase 30 downstream between the pressures. The dual pressures are not limited to downstream movement, however, and can progress upstream or downstream as desired. The dual pressures 160 are shown as rollers that generally move in unison, but can be independently controlled. Other types of suitable pressure application mechanisms may be used instead. By continuously isolating the solid phase 30 from the remainder of the channel 25, contamination of the downstream channel 25 with assay reagents, waste materials and other contaminants is prevented. In addition, movement of the solid phase 30 into a non-contaminated portion of the channel 25 as the diagnostic test progresses, eliminates the need to wash the sidewalls of the channel 25 in addition to washing the solid phase 30 itself, after contact with a reagent.

FIGS. 4a to 4i depict the stages of a diagnostic test process using the disposable diagnostic device 10 of the present invention. The sample transfer area 50, the label 80, and the attachment holes 85 are not shown for clarity. Five pre-filled compartments 35 and three empty compartments 40 are shown arranged on either side of the channel 25.

Figure 4A:
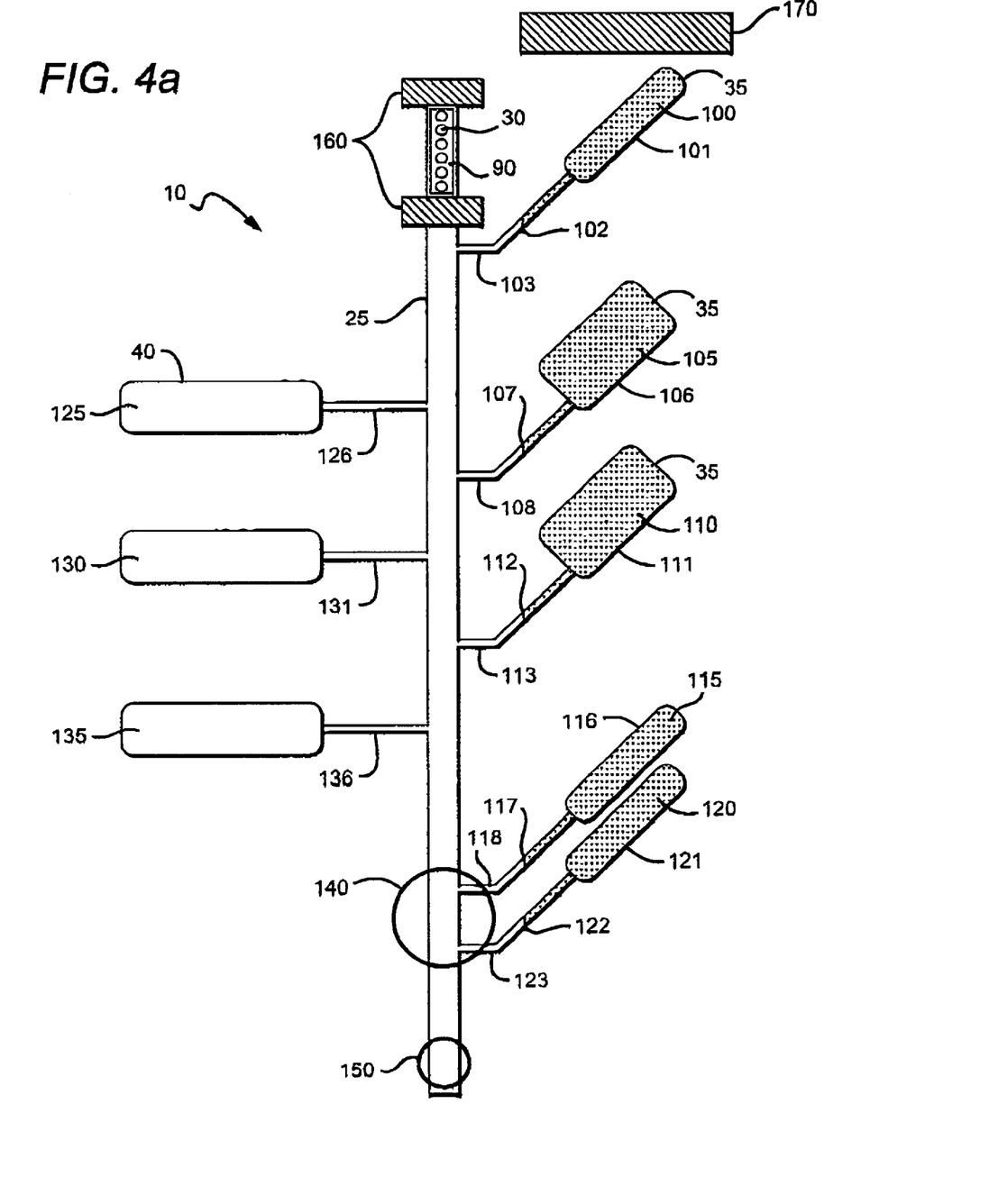
FIGS. 4a–4i are schematic views of the device of FIG. 1 depicting stages of a diagnostic test process.

In FIG. 4a, a sample 90 has already been applied to the solid phase 30 within the channel 25 to start the diagnostic test. Once the sample 90 has been applied, the dual pressures 160, constituting a first peristaltic force, start the solid phase 30 on its journey down the channel 25. A second pressure 170, constituting a second peristaltic force, is in position to apply a single pressure to the pre-filled compartments 35, in the same manner described above for the dual pressures 160 of the first peristaltic force. The second peristaltic force 170 generally is controlled separately from the dual pressures 160, providing versatility in the types of diagnostic tests that can be performed using the diagnostic device 10 of the present invention.

Figure 4B:
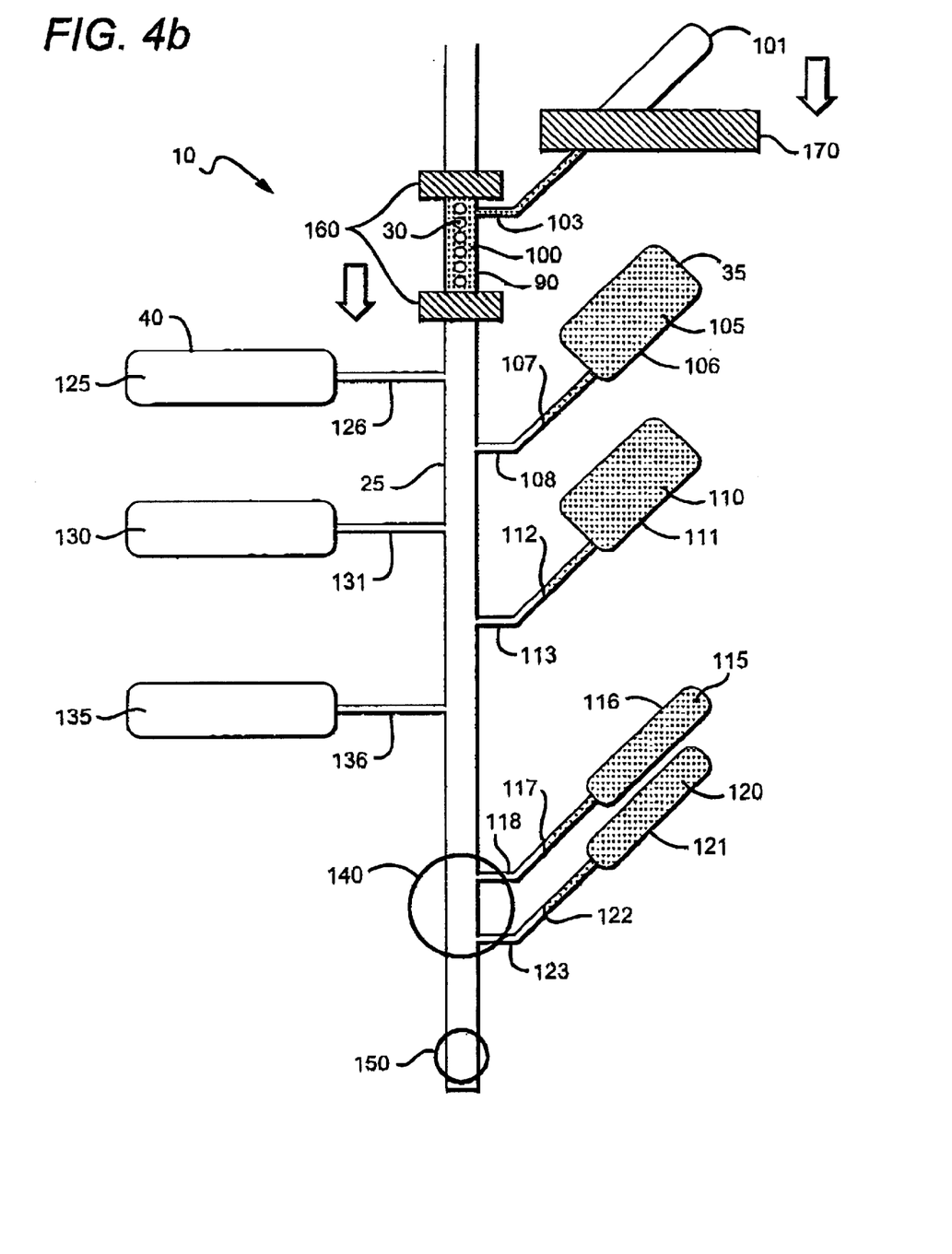

In FIG. 4b, the dual pressures 160 have moved the solid phase 30 downstream, intersecting a connecting passage 103 of the first pre-filled compartment 101. Once this intersection occurs, the second pressure 170 is applied to compartment 101, rupturing a breakable seal 102 (see FIG. 4a), and forcing a fluid 100, such as a tracer or labeled reagent, through connecting passage 103 into the channel 25 at the solid phase 30. The solid phase 30 is now in contact with the sample 90 and the fluid 100.

Figure 4C:
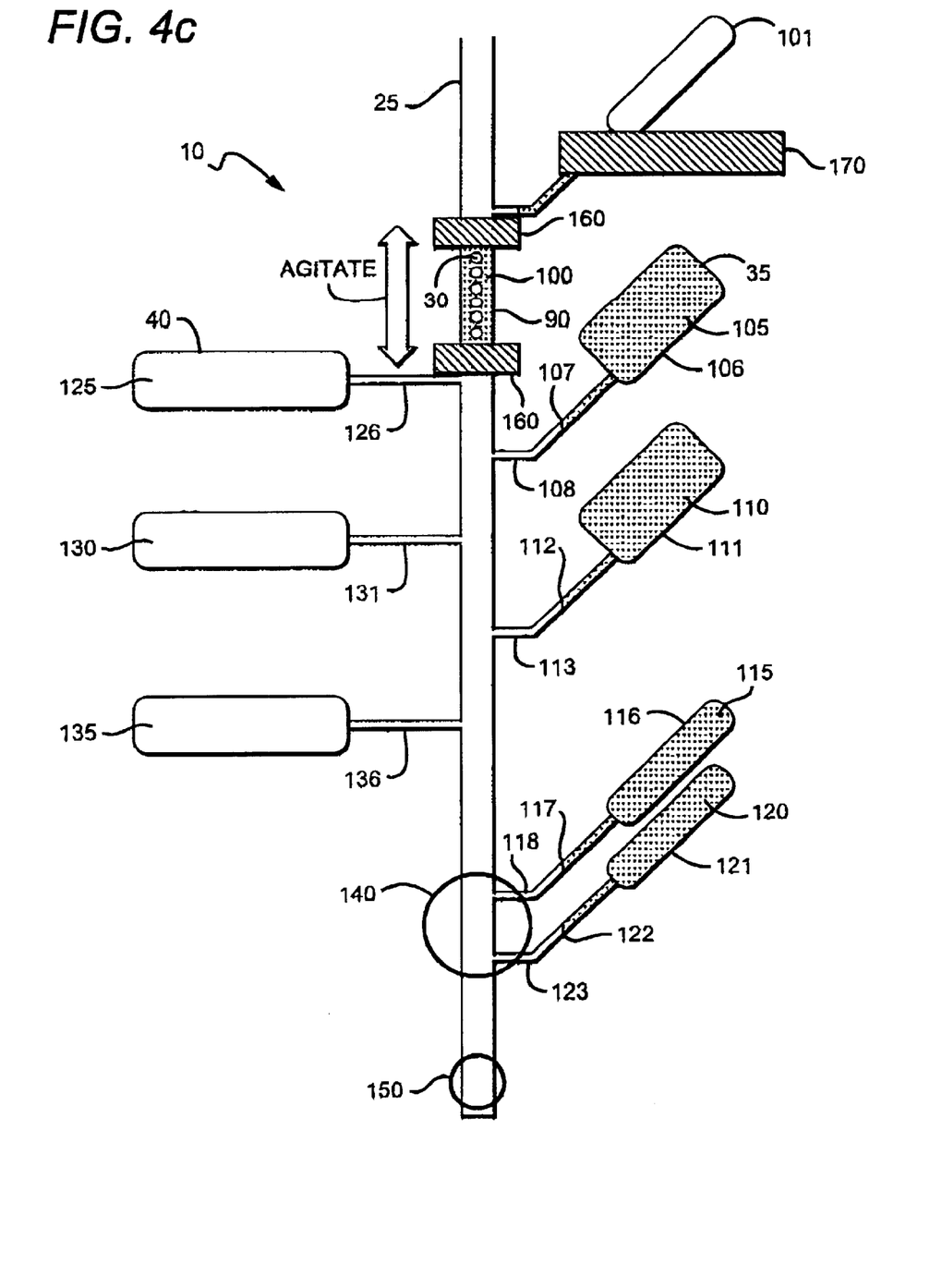

In FIG. 4c, the dual pressures 160 have continued to move the solid phase 30 downstream, past the intersecting connecting passage 103. Once in an isolated position, the solid phase can be agitated by rapid, back and forth movement of the dual pressures 160 for a suitable time period. Agitation decreases the incubation time required for certain diagnostic tests. Agitation can also occur by vibration of the overall device 10, or by other suitable methods, although agitation may not be necessary at all depending on the type of diagnostic test being conducted.

Figure 4D:
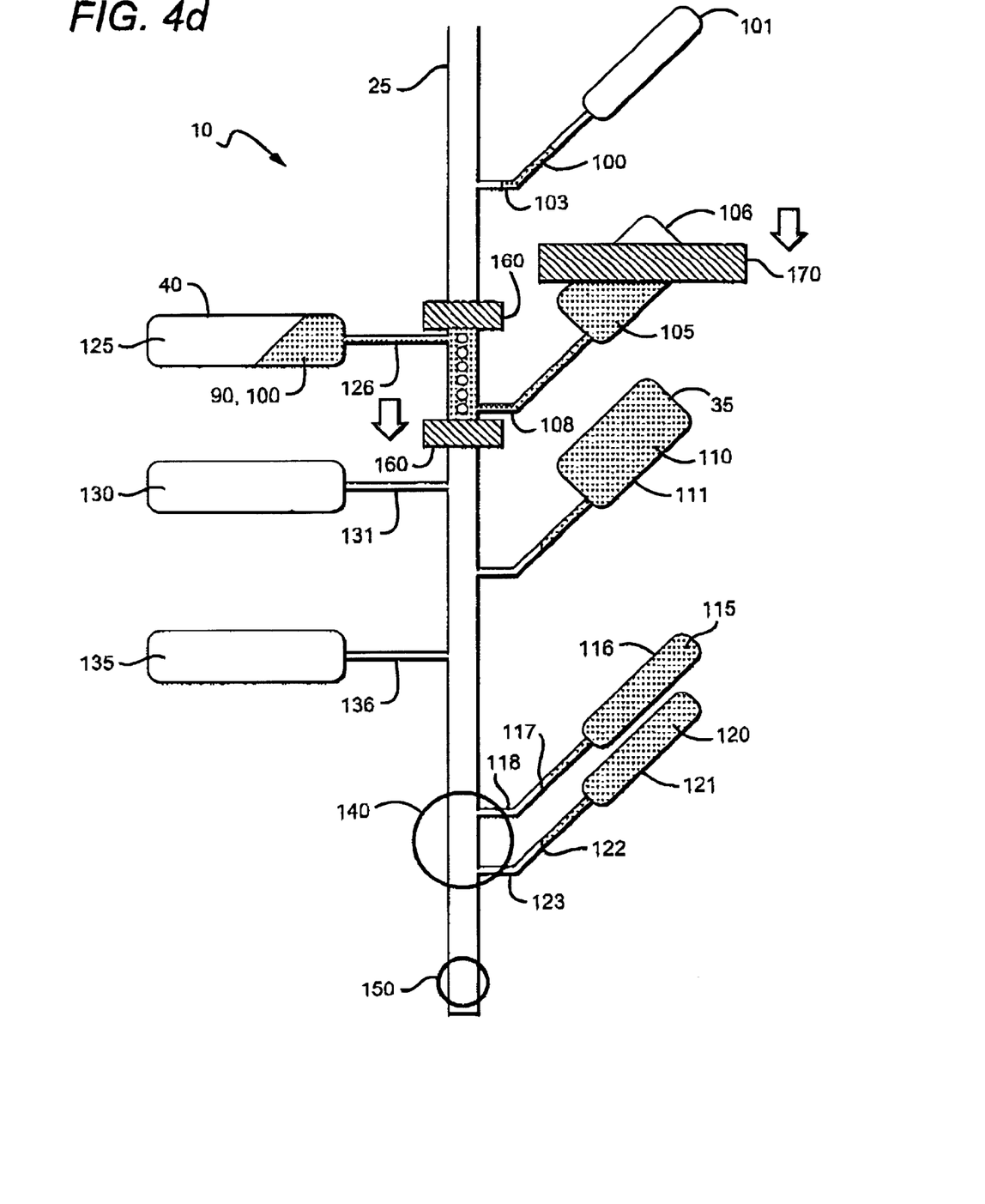

Once incubation is complete, as shown in FIG. 4d, the dual pressures 160 continue moving the solid phase 30 downstream, first intersecting a connecting waste passage 126 and then intersecting a connecting passage 108 from the second pre-filled compartment 106. The second pressure 170 is then applied to compartment 106, rupturing the breakable seal 107 (see FIG. 4a), and forcing a fluid 105, such as a wash fluid, into the channel 25 at the solid phase 30. The pressure of the incoming fluid 105 forces the fluids in contact with the solid phase 90 and 100 upstream, and out of the channel 25 into the first waste compartment 125 through waste passage 126. As the second pressure 170 continues downstream, a portion of the wash fluid 105 is also forced upstream along the solid phase 30 and out of the channel 25 into the waste compartment 125.

Figure 4E:
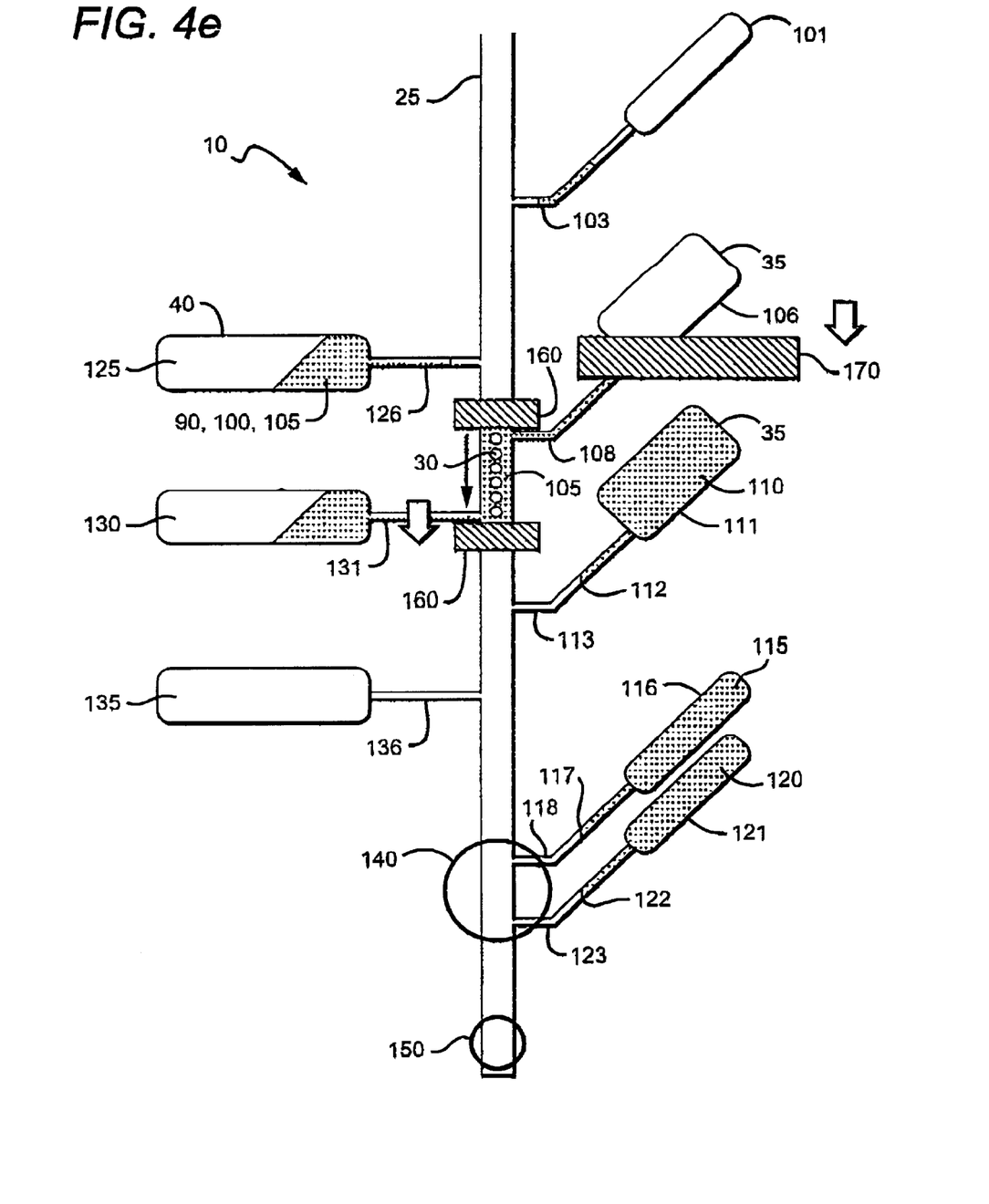

In FIG. 4e, movement of the dual pressures 160 results in the solid phase 30 intersecting a second waste passage 131 connecting a second waste compartment 130 with the channel 25. Continued movement of the second pressure 170 forces the remainder of the wash fluid 105 out of compartment 106 and into the channel 25, along the solid phase 30 downstream and out of the channel 25 into the second waste compartment 130. Movement of the solid phase 30 downstream reverses the direction of the wash fluid 105 as it passes along the solid phase 30, thereby providing a more thorough washing action.

Figure 4F:
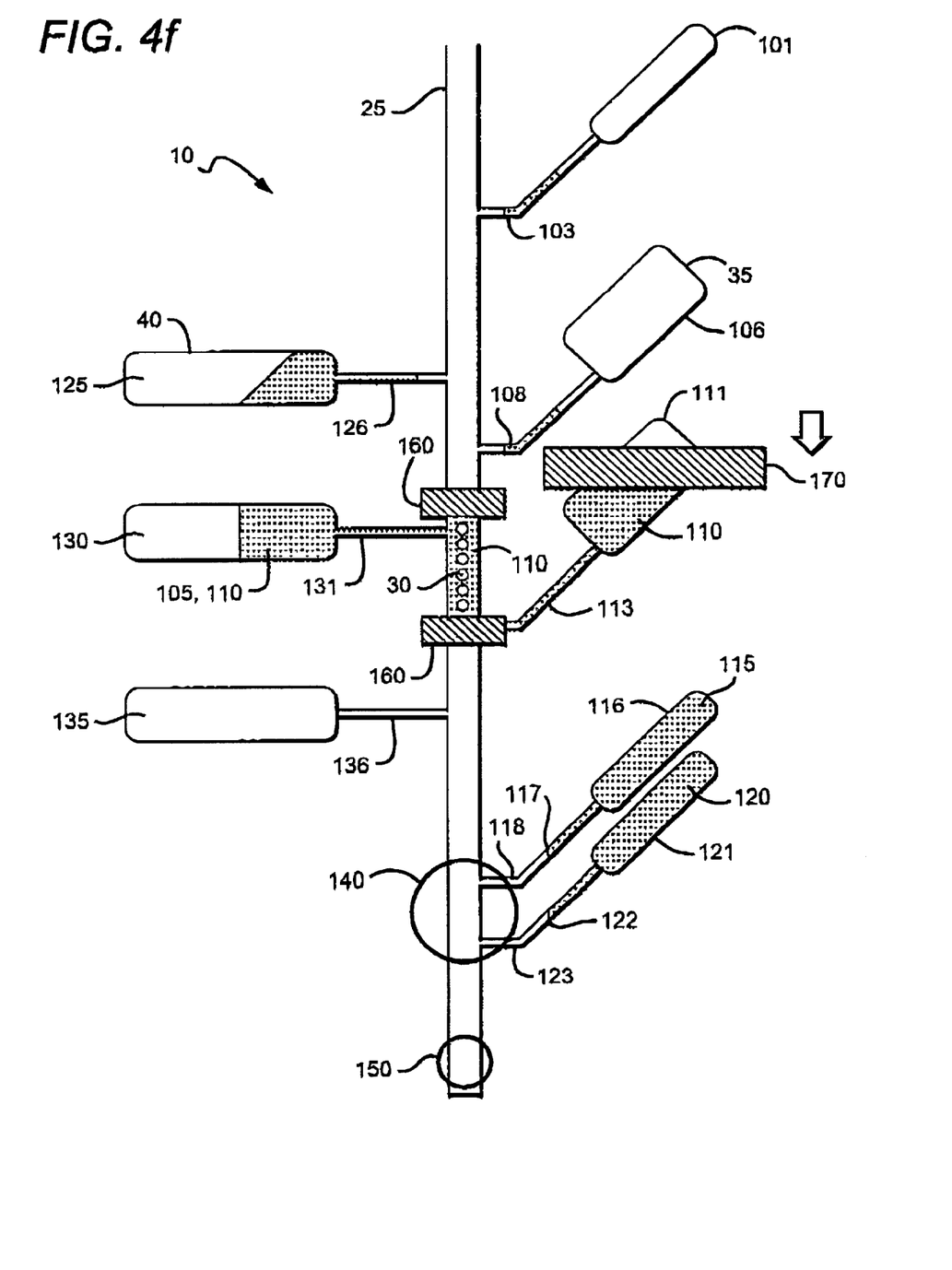

In FIG. 4f, additional downstream movement of the solid phase 30 intersects the solid phase 30 with a third connecting passage 113, connecting the channel 25 to a third pre-filled compartment 111, also filled with a wash fluid 110. The second pressure 170 is then applied to compartment 111 rupturing a breakable seal 112 (see FIG. 4a), and forcing the fluid 110 into the channel 25 at the solid phase 30. Fluid pressure caused by the incoming fluid 110 forces the remainder of fluid 105, along with a portion of the second wash fluid 110, upstream and out of the channel 25 into the second waste compartment 130. Once again, the direction of the fluid flow along the solid phase 30 has reversed.

Figure 4G:
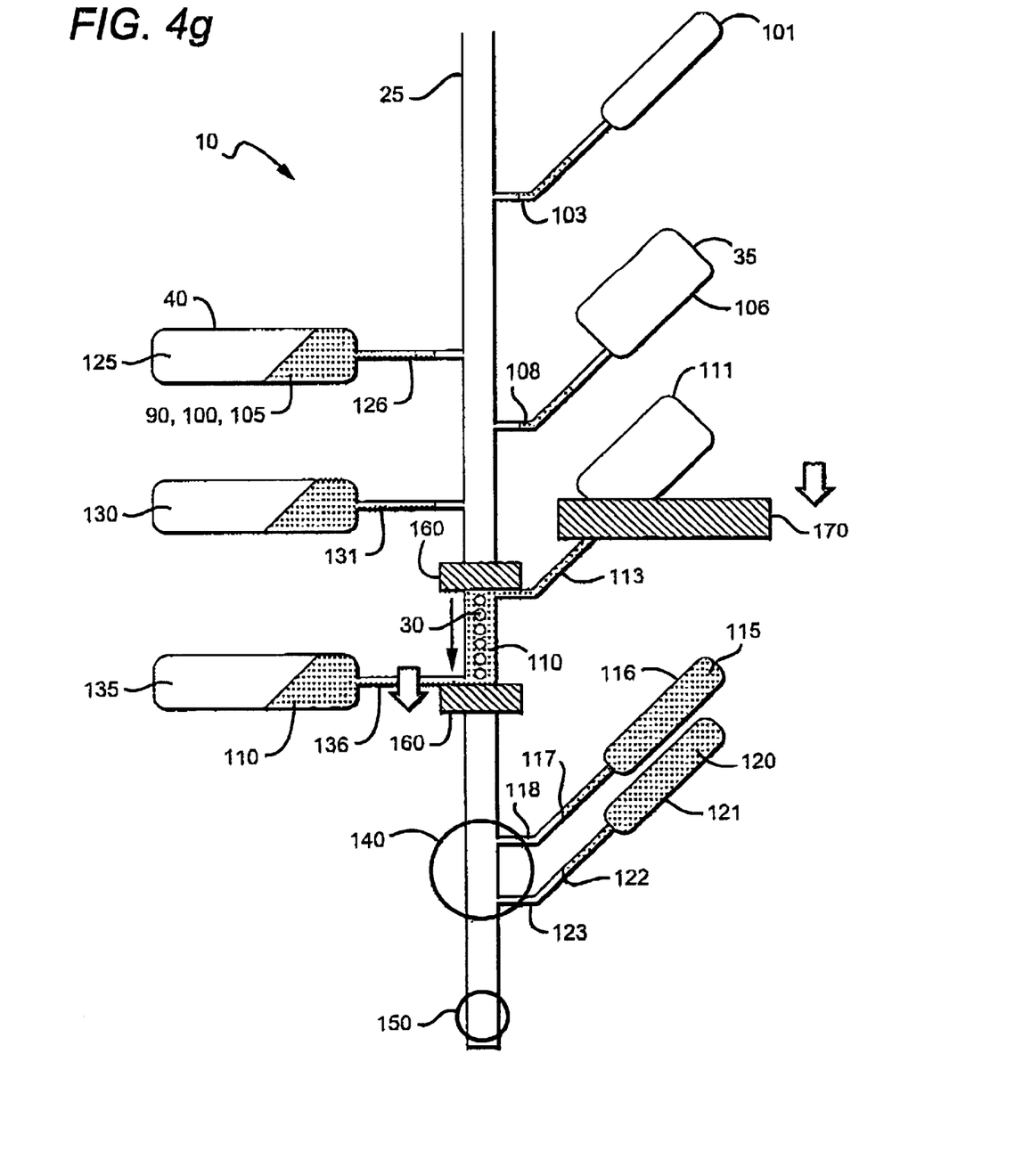

In FIG. 4g, the dual pressures 160 continue downstream resulting in a third waste passage 136 intersecting the solid phase 30. Continued downstream movement of the second pressure 170 forces more of the second wash fluid 110 into the channel 25, downstream, and then out of the channel 25 into a third waste compartment 135 through waste passage 136. Again the fluid flow direction along the solid phase 30 has reversed.

Figure 4H:
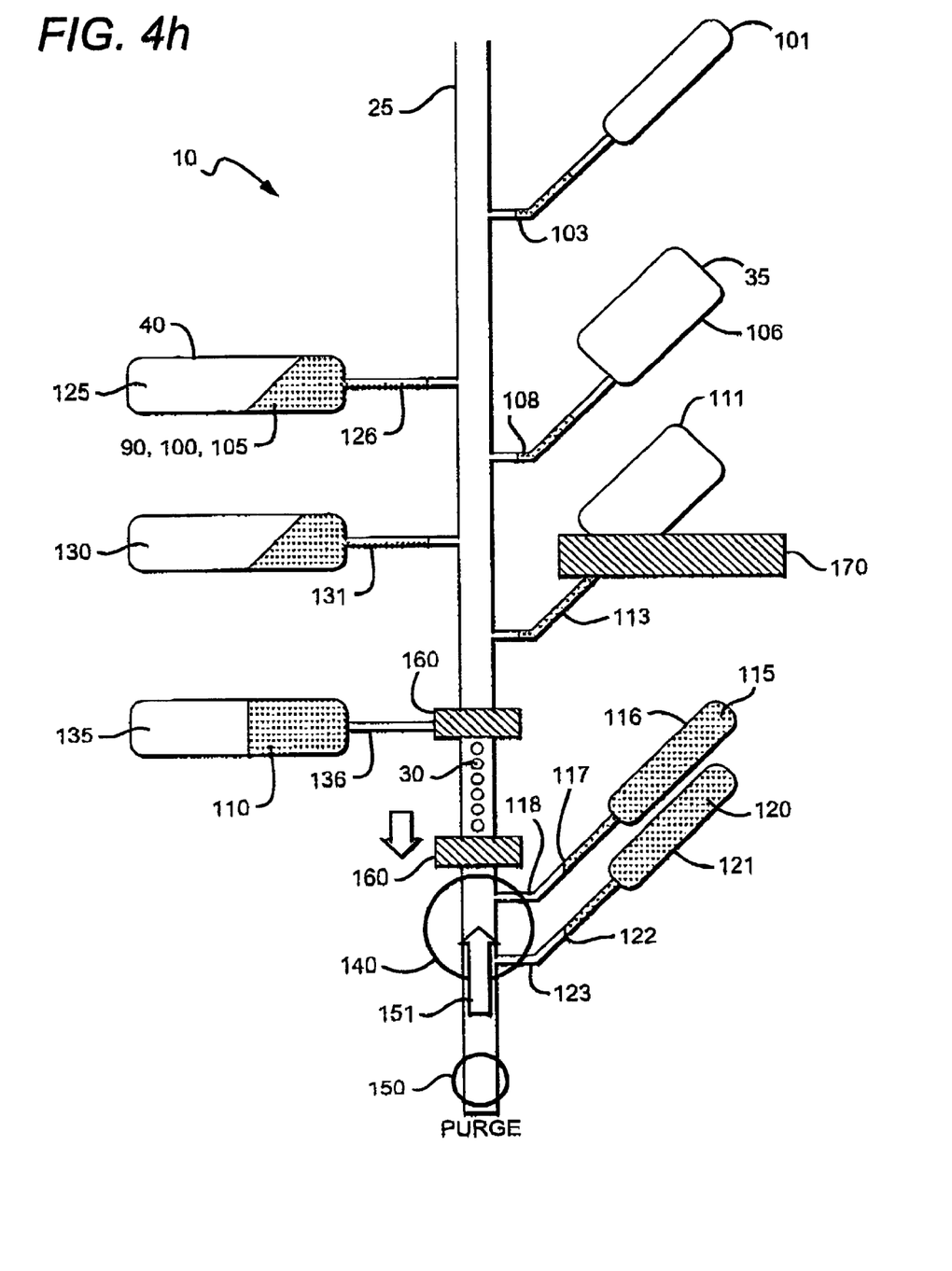

Once the dual pressures 160 have passed the third connecting passage 113, no more fluid pressure is available to force the remainder of the second wash fluid 110 out of the channel 25 and into the third waste compartment 135. In FIG. 4h, an influx of purging air 151 through a dual purpose vent 150 located at the test result end 27 of the channel 25 forces the remainder of the second wash fluid 110 into the third waste compartment 135. The dual purpose vent 150 provides an output for air within the channel 25, as well as an input for external gases that may be necessary for conducting a particular diagnostic test. The downstream pressure roller 161 of the dual pressure 160 is lifted to facilitate the influx of purging air 151 into the channel 25 at the solid phase 30. Removal of all fluid in contact with the solid phase 30 may not be necessary for all types of diagnostic tests.

Figure 4I:
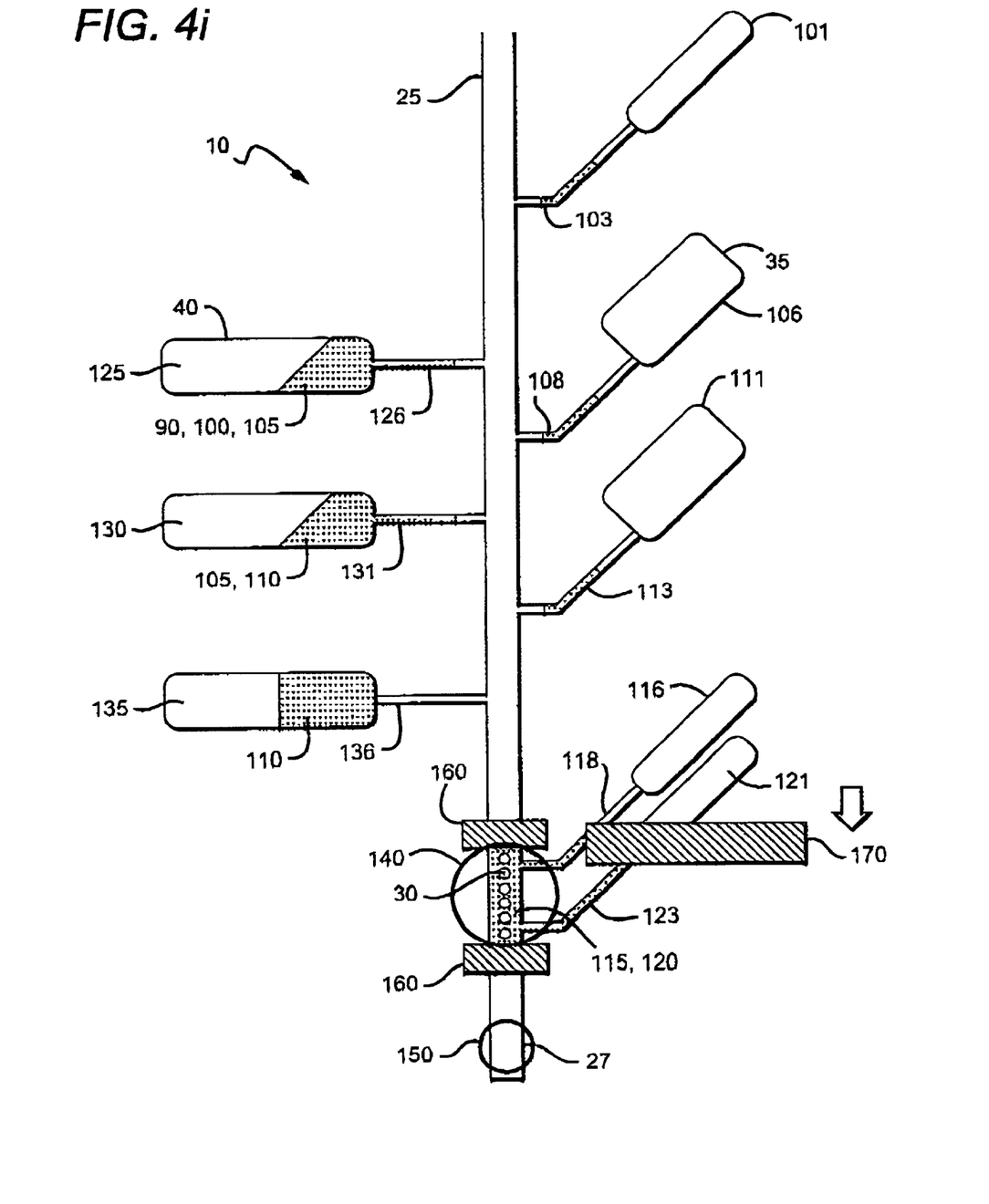

In FIG. 4i, the dual pressures 160 have moved the solid phase 30 into a test result area 140 in which the solid phase 30 intersects two more connecting passages 118 and 123. The test result area 140 may include a transparent detection window within the channel 25 to facilitate detection of the test results. The continued movement of the second pressure 170 applies pressure to both pre-filled compartments 116 and 121, thereby rupturing breakable seals 117 and 122, and forcing detection fluids 115 and 120 into the channel 25 at the solid phase 30. These detection fluids 115 and 120 combine, causing a chemical reaction that facilitates detection of the desired analyte by an external detection device (not shown), such as a photo multiplier tube or PMT.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of manipulating a container, comprising:
    providing a container having a reaction channel fluidly coupled to a plurality of compartments, including a sample receiving compartment and a signal detection compartment, wherein at least one of the compartments includes a reagent;
    introducing a sample into the sample receiving compartment;
    contacting a first portion of a surface of the container with a device having a plurality of independently operable actuators, wherein at least one of the actuators compresses a portion of the container thereby moving at least part of the sample into the reaction channel;
    contacting a second portion of the surface of the container with another one of the actuators that compresses a portion of the container thereby preventing a movement of at least one of the part of the sample and the reagent between at least two of the plurality of compartments; and
    moving the part of the sample in at least one of a unidirectional and bi-directional movement between the sample receiving compartment and the sample detection compartment using the plurality of actuators.

2. The method of claim 1, wherein the container has a flexible top sheet and a flexible bottom sheet, and wherein at least one of the compartments is formed by the flexible top sheet and bottom sheet.

3. The method of claim 1 further comprising aliquoting the sample.

4. The method of claim 1, wherein the sample comprises an analyte and reagent that has a substantially selective binding towards the analyte.

5. The method of claim 1, wherein the reagent is selected from the group consisting of a fluorescent marker, a calorimetric marker, a chemiluminescent marker, an enzymatic marker, and a radioactive marker.

6. The method of claim 1 further comprising providing the container with a waste fluid compartment.

7. The method of claim 6 further comprising providing the container with a second waste fluid compartment.

8. The method of claim 1 further comprising providing the container with a wash supply compartment.

9. The method of claim 1 further comprising detecting a signal in the sample detection compartment.

10. The method of claim 1 further comprising providing the device with a signal detector, and detecting a signal using the signal detector.

11. The method of claim 10 wherein the signal detector comprises a photomultiplier tube.

12. The method of claim 1 further comprising providing a solid phase in the reaction channel.

13. The method of claim 12 wherein the solid phase further comprises an antibody.

14. The method of claim 12 wherein the solid phase further comprises an antigen.

15. The method of claim 12 further comprising combining the solid phase and the sample, and agitating the solid phase by bidirectionally moving the solid phase using the actuators.

* * * * *